US010517804B2

(12) United States Patent
Fei et al.

(10) Patent No.: US 10,517,804 B2
(45) Date of Patent: Dec. 31, 2019

(54) WHITENING COMPOSITIONS AND METHODS FOR INCREASING STABILITY OF THE SAME

(71) Applicant: Colgate-Palmolive Company, New York, NY (US)

(72) Inventors: Lin Fei, Kendall Park, NJ (US); Prakasarao Mandadi, Flemington, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/827,661

(22) Filed: Nov. 30, 2017

(65) Prior Publication Data

US 2019/0159982 A1    May 30, 2019

(51) Int. Cl.
*A61K 8/22* (2006.01)
*A61K 8/24* (2006.01)
*A61Q 11/00* (2006.01)
*A61K 8/34* (2006.01)
*A61K 8/90* (2006.01)
*A61K 8/86* (2006.01)

(52) U.S. Cl.
CPC ............... *A61K 8/22* (2013.01); *A61K 8/24* (2013.01); *A61K 8/34* (2013.01); *A61K 8/345* (2013.01); *A61K 8/86* (2013.01); *A61K 8/90* (2013.01); *A61Q 11/00* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 4,022,881 A | * | 5/1977 | Hawking | A61K 8/731 424/52 |
| 5,374,368 A | | 12/1994 | Hauschild | |
| 5,424,060 A | * | 6/1995 | Hauschild | A61K 8/22 424/52 |
| 8,485,821 B2 | | 7/2013 | Prencipe | |
| 8,591,868 B2 | | 11/2013 | Chopra et al. | |
| 8,865,143 B2 | | 10/2014 | Lu et al. | |
| 9,174,070 B2 | | 11/2015 | Chopra | |
| 9,320,581 B2 | | 4/2016 | Prencipe | |
| 9,439,848 B2 | | 9/2016 | Graham et al. | |
| 10,052,270 B2 | | 8/2018 | Prencipe | |
| 10,299,998 B2 | | 5/2019 | Fei | |
| 2005/0036957 A1 | | 2/2005 | Prencipe | |
| 2007/0071695 A1 | * | 3/2007 | Chopra | A61K 8/20 424/53 |
| 2007/0071696 A1 | | 3/2007 | Wang et al. | |
| 2016/0324740 A1 | * | 11/2016 | Maloney | A61Q 11/00 |
| 2016/0339103 A1 | | 11/2016 | Wang et al. | |

FOREIGN PATENT DOCUMENTS

| | | |
|---|---|---|
| EP | 0868903 | 10/1998 |
| WO | 2005/016299 | 2/2005 |
| WO | 2012/102750 | 8/2012 |
| WO | 2014/092735 | 6/2014 |
| WO | 2017/087442 | 5/2017 |

OTHER PUBLICATIONS

SD Singh-Joy, VC McLain. International Journal of Toxicology, vol. 27(Suppl 2), 2008, pp. 93-128. (Year: 2008).*
M Putt. "Abrasion, Polishing, and Stain Removal Characteristics of Various Commercial Dentifrices In Vitro." The Journal of Clinical Dentistry, vol. XXII, No. 1, 2011, pp. 11-18. (Year: 2011).*
International Search Report and Written Opinion of the International Searching Authority in International Application No. PCT/US2017/063939, dated Aug. 7, 2018.

* cited by examiner

*Primary Examiner* — Isaac Shomer

(57) ABSTRACT

Oral care compositions and methods for whitening and preventing stains on teeth are provided. The oral care composition may include an orally acceptable vehicle, a peroxide whitening agent, and an abrasive system. The orally acceptable vehicle may include a block copolymer of ethylene oxide and propylene oxide, and the abrasive system may include at least one insoluble phosphate salt.

14 Claims, No Drawings

WHITENING COMPOSITIONS AND METHODS FOR INCREASING STABILITY OF THE SAME

BACKGROUND

Conventional oral care products or compositions thereof (e.g., toothpastes, gels, etc.) including peroxide whitening agents are often utilized to whiten teeth. For example, conventional toothpastes including peroxides (e.g., hydrogen peroxide) are often utilized to oxidize chromophores bound to surfaces of teeth to thereby whiten the teeth. The peroxides, however, are often unstable (e.g., reactive) and subject to degradation.

In view of the foregoing, the peroxides in the oral care products and/or compositions are often combined with components that aid and/or facilitate the stabilization of the peroxides. While conventional stabilizing components have proven to be effective for stabilizing the peroxides, the effectiveness of conventional stabilizing components is still limited due to the relatively high reactivity of the peroxides.

What is needed, then, are improved oral care compositions including peroxide whitening agents and methods for improving stability of the peroxide whitening agents in the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide an oral care composition including an orally acceptable vehicle, a peroxide whitening agent, and an abrasive system. The orally acceptable vehicle may include a block copolymer of ethylene oxide and propylene oxide. The abrasive system may include at least one insoluble phosphate salt.

In at least one embodiment, the oral care composition may include water in an amount of less than 5 weight %, less than 3 weight %%, less than 1.0 weight %, less than 0.1 weight %, less than 0.05 weight %, less than 0.01 weight %, less than 0.005 weight %, or less than 0.0001 weight %, based on a total weight of the oral care composition. For example, the oral care composition may be anhydrous.

In at least one embodiment, the orally acceptable vehicle may further include a humectant. The humectant may include at least one of glycerin, propylene glycol, polyethylene glycol, and combinations thereof.

In at least one embodiment, the orally acceptable vehicle may only include the block copolymer of ethylene oxide and propylene oxide and propylene glycol.

In at least one embodiment, the block copolymer of ethylene oxide and propylene oxide may be represented by formula (ethylene oxide)$_x$-(propylene oxide)$_y$-(ethylene oxide)$_z$, where x may be an integer from about 5 to about 15, y may be an integer from about 10 to about 20, and z may be an integer from about 5 to about 15.

In at least one embodiment, the block copolymer of ethylene oxide and propylene oxide may be represented by formula (ethylene oxide)$_{11}$-(propylene oxide)$_{16}$-(ethylene oxide)$_{11}$.

In at least one embodiment, the block copolymer of ethylene oxide and propylene oxide may have an average molecular weight greater than or equal to about 1,000 Da and less than or equal to about 3,000 Da.

In at least one embodiment, the block copolymer of ethylene oxide and propylene oxide may be present in an amount of from about 5 weight % to about 60 weight %, preferably about 22 weight % to about 25 weight %, more preferably about 23 weight %, based on a total weight of the oral care composition.

In at least one embodiment, the orally acceptable vehicle includes the propylene glycol and the block copolymer of ethylene oxide and propylene oxide in a weight ratio of from about 0.9:1 to about 1.1:1, preferably about 1:1.

In at least one embodiment, the abrasive system includes at least one of sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, or mixtures thereof.

In at least one embodiment, the abrasive system consists essentially of sodium metaphosphate and calcium pyrophosphate.

In at least one embodiment, the abrasive system consists of sodium metaphosphate and calcium pyrophosphate.

In at least one embodiment, a weight ratio of the sodium metaphosphate to the calcium pyrophosphate may be from about 0.5:1 to about 2.9:1, about 1.6:1 to about 1.8:1, more preferably about 1.7:1.

In at least one embodiment, the abrasive system may be present in an amount of from about 5 weight % to about 40 weight %, about 18 weight % to about 22 weight %, preferably about 19 weight % to about 21 weight %, or more preferably about 20 weight %, based on a total weight of the oral care composition.

Embodiments of the disclosure may provide a method for whitening teeth. The method may include contacting any one of the oral care compositions disclosed herein with a surface of the teeth.

Embodiments of the disclosure may provide a method for preventing stains on teeth. The method may include contacting any one of the oral care compositions disclosed herein with a surface of the teeth.

Embodiments of the disclosure may provide a method for increasing peroxide stability in an oral care composition. The method may include replacing at least a portion of an orally acceptable vehicle with a block copolymer of ethylene oxide and propylene oxide represented by the formula (ethylene oxide)$_{11}$-(propylene oxide)$_{16}$-(ethylene oxide)$_{11}$. The method may also include combining the orally acceptable vehicle with an abrasive system including a combination of sodium metaphosphate and calcium pyrophosphate.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that oral care products and/or oral care compositions thereof including the combination of an orally acceptable vehicle or liquid carrier having a block copolymers of ethylene oxide (EO) and propylene oxide (PO), and an abrasive system having insoluble phosphates, exhibits increased peroxide stability as compared conventional oral care products and/or oral care compositions thereof. The present inventors have also surprisingly and unexpectedly discovered that the oral care products and/or oral care compositions thereof may exhibit increased peroxide stability while maintaining teeth cleaning performance or pellicle cleaning ratio (PCR) greater than or equal to 80. The present inventors have also surprisingly and unexpectedly discovered a method of increasing peroxide stability in an oral care product and/or an oral care composition thereof. The method of increasing peroxide stability may include replacing at least a portion of a conventional orally acceptable vehicle or liquid carrier, such as propylene glycol, polyethylene glycol, and/or glycerin with a block copolymers of ethylene oxide (EO) and propylene oxide (PO) and the abrasive system. It should be appreciated that the increased peroxide stability in the oral care products and/or oral care compositions thereof are achieved without encapsulations and/or film-type materials to enhance the stability thereof.

Compositions disclosed herein may be or include an oral care product and/or an oral care composition thereof. The oral care composition may be a non-aqueous oral care composition, such as a non-aqueous dentifrice or toothpaste. The oral care composition may include an orally acceptable vehicle, one or more peroxide whitening agents, and an abrasive system. The orally acceptable vehicle may include one or more block copolymers of ethylene oxide and propylene oxide, the peroxide whitening agents may include hydrogen peroxide and/or one or more sources of hydrogen peroxide, and the abrasive system may include one or more insoluble phosphates or phosphate salts. In an exemplary implementation, the orally acceptable vehicle includes propylene glycol and the block copolymer of ethylene oxide and propylene oxide, the peroxide whitening agents include hydrogen peroxide or one or more sources of hydrogen peroxide, and the abrasive system includes alkali and/or alkali earth metal phosphate salts, such as sodium metaphosphate and/or calcium pyrophosphate.

The oral care composition prior to use may be anhydrous. For example, the oral care composition may be free or substantially free of water. As used herein, "free of water" or "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition. The oral care composition prior to use may have a "low water content". As used herein, "low water content" may refer to a composition that contains water in an amount greater than about 5 weight % and less than about 7 weight % or less than about 10 weight %.

The oral care product or the oral care composition thereof may be a single phase oral care product or oral care composition. For example, the orally acceptable vehicle, the one or more peroxide whitening agents, and the abrasive system may all be maintained together with one another in a single phase and/or vessel. For example, the orally acceptable vehicle, the one or more peroxide whitening agents, and the abrasive system may all be maintained in a single phase, such as a single homogenous phase. The single homogenous phase including the orally acceptable vehicle, the one or more peroxide whitening agents, and the abrasive system may be an anhydrous formulation or an anhydrous composition.

The oral care composition may form at least a portion of or be used in one or more oral care products. The oral care composition may include or be combined with an orally acceptable vehicle to form the oral care product (e.g., the toothpaste). Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may form at least a portion of or be used with a toothpaste. For example, the oral care composition may typically be a gel of the toothpaste, or a whitening gel to be combined with the toothpaste. The oral care composition may include or be combined with an orally acceptable vehicle to form the oral care product (e.g., the toothpaste).

In at least one implementation, the orally acceptable vehicle may include one or more humectants. Illustrative humectants may be or include, but are not limited to, glycerin, propylene glycol, polyethylene glycol, and combinations thereof. In a preferred implementation, the orally acceptable vehicle may be or include, but is not limited to, propylene glycol. The propylene glycol may be present in an amount of from 5 weight % to about 60 weight %, based on a total weight of the oral care composition. For example, the propylene glycol may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the propylene glycol may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the propylene glycol may be present in an amount of about 20 weight % to about 30 weight %, preferably about 20 weight % to about 25 weight %, and more preferably about 22 weight % to about 25 weight %. In a preferred implementation, the propylene glycol may be present in an amount of about 22 weight % to about 25 weight % or about 23 weight %.

In an exemplary implementation, the orally acceptable vehicle may be or include one or more block copolymers of ethylene oxide (EO) and propylene oxide (PO). The block copolymers of ethylene oxide and propylene oxide may be nonionic. For example, the block copolymers of ethylene oxide and propylene oxide may be a nonionic surfactant. The block copolymers of ethylene oxide and propylene oxide may be represented by formula (1)

$$(\text{ethylene oxide})_x\text{-(propylene oxide)}_y\text{-(ethylene oxide)}_z \quad (1)$$

where x may be an integer of from about 5 to about 15 (e.g., x=9-13, or about 11), y may be an integer from about 10 to about 20 (e.g., y=13-17, or about 16), and z may be an integer from about 5 to about 15 (e.g., x=9-13, or about 11). In another implementation, x may be an integer from about 2 to about 65, y may be an integer from about 15 to about 70, and z may be an integer from about 2 to about 65. In an exemplary implementation, the block copolymer of ethylene oxide and propylene oxide may be represented by formula (2).

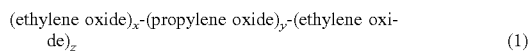
$$(\text{ethylene oxide})_{11}\text{-(propylene oxide)}_{16}\text{-(ethylene oxide)}_{11} \quad (2)$$

The block copolymer of ethylene oxide and propylene oxide may have an average molecular weight greater than or equal to about 1,000 Da and less than or equal to about 3,000 Da. For example, the block copolymer of ethylene oxide and propylene oxide may have an average molecular weight of from about 1,000 Da, about 1,100 Da, about 1,200 Da, about 1,300 Da, about 1,400 Da, about 1,500 Da, about 1,600 Da, about 1,700 Da, about 1,800 Da, or about 1,850 Da to about 1,950 Da, about 2,000 Da, about 2,100 Da, about 2,200 Da, about 2,300 Da, about 2,400 Da, about 2,500 Da, about 2,600 Da, about 2,700 Da, about 2,800 Da, about 2,900 Da, or about 3,000 Da. In another example, the block copolymer of ethylene oxide and propylene oxide may have an average molecular weight of from about 1,000 Da to about 2,800 Da, about 1,100 Da to about 2,700 Da, about 1,200 Da to about 2,600 Da, about 1,300 Da to about 2,500 Da, about 1,400 Da to about 2,400 Da, about 1,500 Da to about 2,300 Da, about 1,600 Da to about 2,200 Da, about 1,700 Da to about 2,100 Da, about 1,800 Da to about 2,000 Da, or about 1,850 Da to about 1,950 Da. In an exemplary implementation, the block copolymer of ethylene oxide and propylene oxide may have an average molecular weight of about 1,850 Da to about 1,950 Da, preferably about 1,900 Da.

Illustrative block copolymers of ethylene oxide (EO) and propylene oxide (PO) may be or include, but are not limited to, PLURONIC® L1, PLURONIC® L43, PLURONIC® L10, PLURONIC® L44, PLURONIC® 10R5, PLURONIC® 17R4, PLURONIC® L25R4, PLURONIC® P84, PLURONIC® P65, PLURONIC® P104, PLURONIC® P105, and the like, and combinations thereof, all of which are commercially available from BASF of Mount Olive, N.J. Other exemplary block copolymers may be or include, but are not limited to, those exemplified in Table 1. In a typical implementation, the orally acceptable vehicle includes PLURONIC® L-35.

TABLE 1

Exemplary Block Copolymers of EO and PO

| Pluronic | Formula | MW (Da) |
|---|---|---|
| L31 | $EO_2\text{—}PO_6\text{—}EO_2$ | 1100 |
| L35 | $EO_{11}\text{—}PO_{16}\text{—}EO_{11}$ | 1900 |
| L61 | $EO_2\text{—}PO_{31}\text{—}EO_2$ | 2000 |
| L44 | $EO_{10}\text{—}PO_{23}\text{—}EO_{10}$ | 2200 |
| L62 | $EO_6\text{—}PO_{35}\text{—}EO_6$ | 2500 |
| L64 | $EO_{13}\text{—}PO_{30}\text{—}EO_{13}$ | 2900 |
| L81 | $EO_3\text{—}PO_{43}\text{—}EO_3$ | 2750 |
| L10 | $EO_4\text{—}PO_{50}\text{—}EO_4$ | 3200 |
| L92 | $EO_8\text{—}PO_{50}\text{—}EO_8$ | 3650 |
| L121 | $EO_5\text{—}PO_{68}\text{—}EO_5$ | 4400 |
| P85 | $EO_{26}\text{—}PO_{40}\text{—}EO_{26}$ | 4600 |
| P123 | $EO_{20}\text{—}PO_{69}\text{—}EO_{20}$ | 5750 |
| F87 | $EO_{61}\text{—}PO_{40}\text{—}EO_{61}$ | 7700 |

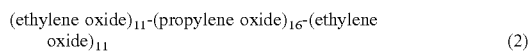

The amount or concentration of the block copolymer of ethylene oxide and propylene oxide may vary widely. In at least one example, the block copolymer of ethylene oxide and propylene oxide may be present in an amount of from 5 weight % to about 60 weight %, based on a total weight of the oral care composition. For example, the block copolymer of ethylene oxide and propylene oxide may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the block copolymer of ethylene oxide and propylene oxide may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the block copolymer of ethylene oxide and propylene oxide may be present in an amount of about 20 weight % to about 30 weight %, preferably about 20 weight % to about 25 weight %, and more preferably about 22 weight % to about 25 weight %. In a preferred implementation, the block copolymer of ethylene oxide and propylene oxide may be present in an amount of about 22 weight % to about 25 weight % or about 23 weight %.

In at least one implementation, the weight ratio of the propylene glycol to the block copolymer of ethylene oxide and propylene oxide in the orally acceptable vehicle may be greater than or equal to about 0.5:1 and less than or equal to 1.5:1. For example, the weight ratio of the propylene glycol to the block copolymer of ethylene oxide and propylene oxide in the orally acceptable vehicle may be from about 0.5:1, about 0.6:1, about 0.7:1, about 0.8:1, or about 0.9:1 to about 1.1:1, about 1.2:1, about 1.3:1, about 1.4:1, about 1.5:1. In another example, the weight ratio of the propylene glycol to the block copolymer of ethylene oxide and propylene oxide in the orally acceptable vehicle may be from about 0.5:1 to about 1.5:1, about 0.6:1 to about 1.4:1, about 0.7:1 to about 1.3:1, about 0.8:1 to about 1.2:1, or about 0.9:1 to about 1.1:1. In an exemplary implementation, the weight ratio of the propylene glycol to the block copolymer of ethylene oxide and propylene oxide in the orally acceptable vehicle may be from about 0.9:1 to about 1.1:1, preferably about 1:1.

The oral care product or the composition thereof may include one or more peroxide whitening agents. The peroxide whitening agents may be or include, but are not limited to, hydrogen peroxide or one or more sources of hydrogen peroxide. For example, the peroxide whitening agents may be hydrogen peroxide and/or hydrogen peroxide releasing substances. The one or more sources of hydrogen peroxide may be or include any compound or material configured to release hydrogen peroxide. Preferably, the peroxide whitening agents include, but are not limited to, solid peroxide whitening agents and bound peroxide whitening agents which are substantially anhydrous oxygen generating compounds. Solid peroxide whitening agents may include, but are not limited to, peroxides and persulfates. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The peroxide whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some implementations, it may be desirable to use any known peroxide whitening agent except sodium percarbonate and/or any of the percarbonate salts. The sources of hydrogen peroxide or peroxide whitening agents may also be or include, but are not limited to, PEROXYDONE™ XL 10 complex or POLYPLASDONE® XL 10F, which are commercially available from Ashland Inc. of Covington, Ky. In a typical implementation, the source of hydrogen peroxide includes a cross-linked PVP hydrogen peroxide complex.

The amount or concentration of the source of hydrogen peroxide may vary widely. In at least one example, the source of hydrogen peroxide may be present in an amount that provides a concentration of hydrogen peroxide of less than or equal to 4 weight %, less than or equal to 3.5 weight %, less than or equal to 3 weight %, less than or equal to 2.5 weight %, less than or equal to 2 weight %, or less than or equal to 1.5 weight %, based on a total weight of the oral care product or the composition thereof. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 1 weight %, about 3 weight %, about 5 weight %, about 7 weight %, about 9 weight %, about 11 weight %, about 13 weight %, or about 15 weight % to about 17 weight %, about 19 weight %, about 21 weight %, about 23 weight %, about 25 weight %, about 27 weight %, about 29 weight %, or about 30 weight %. In another example, the source of hydrogen peroxide may be present in an amount of from about 1 weight % to about 30 weight %, about 3 weight % to about 29 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In a preferred implementation, the source of hydrogen peroxide is a cross-linked PVP complexed with hydrogen peroxide, and is present in an amount of from about 8 weight % to about 14 weight %, preferably about 10 weight % to about 12 weight %, and more preferably about 11 weight %.

The oral care product or the composition thereof may include an abrasive system including one or more abrasives. As used herein, the term "abrasive" may also refer to materials commonly referred to as "polishing agents". Illustrative abrasives may include, but are not limited to, one or more phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, and the like, and mixtures or combinations thereof. In at least one implementation, the abrasives may include a combination of one or more phosphate salts and an additional abrasive. Illustrative abrasives that may be combined with the phosphate salts may be or include, but are not limited to, calcium carbonate, magnesium carbonate, hydrated alumina, silica, zircconium silicate, aluminum silicate including calcined aluminum silicate, polymethyl methacrylate, and the like, and mixtures or combinations thereof. In an exemplary implementation, the abrasive system includes a combination of abrasives. For example, the abrasive system may include a combination of sodium metaphosphate and calcium pyrophosphate.

The amount or concentration of the abrasive system and abrasives thereof may vary widely. In at least one implementation, the amount or concentration of the abrasives may be from about 5 weight % to about 40 weight %, based on a total weight of the oral care product or the composition thereof. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 18 weight % to about 22 weight %, preferably about 19 weight % to about 21 weight %, or more preferably about 20 weight %.

In at least one implementation, the abrasive system includes sodium metaphosphate and calcium pyrophosphate, and the weight ratio of the sodium metaphosphate to the calcium pyrophosphate may be greater than or equal to about 0.5:1 and less than 2.9:1. For example, the weight ratio of the sodium metaphosphate to the calcium pyrophosphate may be from about 0.5:1, about 0.6:1, about 0.7:1, about 0.8:1, about 0.9:1, about 1:1, about 1.1:1, about 1.2:1, about 1.3:1, about 1.4:1, about 1.5:1, or about 1.6:1 to about 1.8:1, about 1.9:1, about 2.0:1, about 2.1:1, about 2.2:1, about 2.3:1, about 2.4:1, about 2.5:1, about 2.6:1, about 2.7:1, about 2.8:1, or about 2.9:1. In another example, the weight ratio of the sodium metaphosphate to the calcium pyrophosphate may be from about 0.5:1 to about 2.9:1, about 0.6:1 to about 2.8:1, about 0.7:1 to about 2.7:1, about 0.8:1 to about 2.6:1, about 0.9:1 to about 2.5:1, about 1:1 to about 2.4:1, about 1.1:1 to about 2.3:1, about 1.2:1 to about 2.2:1, about 1.3:1 to about 2.1:1, about 1.4:1 to about 2.0:1, about 1.5:1 to about 1.9:1, or about 1.6:1 to about 1.8:1. In a preferred implementation, the weight ratio of the sodium metaphosphate to the calcium pyrophosphate may be from about 1.6:1 to about 1.8:1, more preferably about 1.7:1.

In another implementation, the abrasive system includes sodium metaphosphate and calcium pyrophosphate, and the weight ratio of the sodium metaphosphate to the calcium pyrophosphate may be greater than or equal to about 2.6:1 and less than 5:1. For example, the weight ratio of the sodium metaphosphate to the calcium pyrophosphate may be from about 2.6:1, about 2.7:1, about 2.8:1, about 2.9:1, about 3:1, about 3.1:1, about 3.2:1, about 3.3:1, about 3.4:1, about 3.5:1, about 3.6:1, or about 3.7:1 to about 3.9:1, about 4:1, about 4.1:1, about 4.2:1, about 4.3:1, about 4.4:1, about 4.5:1, about 4.6:1, about 4.7:1, about 4.8:1 about 4.9:1, or about 5:1. In another example, the weight ratio of the sodium metaphosphate to the calcium pyrophosphate may be from about 2.6:1 to about 5:1, about 2.7:1 to about 4.9:1, about 2.8:1 to about 4.8:1, about 2.9:1 to about 4.7:1, about 3:1 to about 4.6:1, about 3.1:1 to about 4.5:1, about 3.2:1 to about 4.4:1, about 3.3:1 to about 4.3:1, about 3.4:1 to about 4.2:1, about 3.5:1 to about 4.1:1, about 3.6:1 to about 4:1, or about 3.7:1 to about 3.9:1. In a preferred implementation, the weight ratio of the sodium metaphosphate to the calcium pyrophosphate may be from about 3.7:1 to about 3.9:1, more preferably about 3.8:1.

In at least one implementation, the oral care products and/or the oral care composition thereof may be free or substantially free of fluoride (e.g., soluble fluoride salts). In another implementation, the oral care products and/or the oral care composition thereof may further include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium monofluorophosphate. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

It should be appreciated to one having ordinary skill in the art, that the oral care products and/or the oral care composition thereof may include other additional ingredients/components. For example, the oral care products and/or the oral care composition thereof may include anti-caries agents, desensitizing agents, viscosity modifiers, diluents, pH modifying agents, humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent. Generally, anticalculus agents may not be compatible with some oral care composition, however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

The oral care product or the compositions thereof may have a pellicle cleaning ratio (PCR) of greater than 75, greater than 76, greater than 77, greater than 78, greater than 79, greater than 80, greater than 81, greater than 82, greater than 83, greater than 84, greater than 85, greater than 86, greater than 87, greater than 88, greater than 89, greater than 90, greater than 91, greater than 92, greater than 93, greater than 94, greater than 95, greater than 96, greater than 97, greater than 98, greater than 99, or greater than 100. In a preferred implementation, the oral care product or the compositions thereof may have a pellicle cleaning ratio (PCR) of greater than 80, preferably greater than 85, more preferably greater than or equal to 88.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

The present disclosure may provide methods for increasing peroxide stability in an oral care product and the oral care composition thereof. The method may include combining, mixing, or otherwise contacting an orally acceptable vehicle including propylene glycol and a block copolymer of ethylene oxide and propylene oxide with an abrasive system including sodium metaphosphate and calcium pyrophosphate. The method may also include replacing at least a portion of an orally acceptable vehicle or liquid carrier of a conventional oral care composition (e.g., propylene glycol, polyethylene glycol, and/or glycerin) with a block copolymers of ethylene oxide (EO) and propylene oxide (PO), and combining the orally acceptable vehicle with the abrasive system. The method may include at least partially preventing the peroxide whitening agent or peroxides from reacting with other components of the oral care composition under accelerated aging conditions (e.g., temperature from about 40° C. to about 50° C.). The method may also include at least partially preventing the peroxide whitening agent or peroxides from reacting with other components of the oral care composition for at least three months under accelerated aging conditions. The method may further include maintaining viability, stability, and/or compatibility with the peroxide whitening agent under accelerated aging conditions. For example, the method may include maintaining viability, stability, and/or compatibility with the peroxide whitening agent for at least three months.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Four oral care compositions (1)-(4), including a control oral care composition (1) and three test compositions (2)-(4), were evaluated. The oral care compositions (1)-(4) were prepared by combining the ingredients/components (weight %) according to Table 2. It should be appreciated that each of the oral care compositions (1)-(4) contained 2 weight % of hydrogen peroxide, as delivered from the cross-linked PVP complexed with hydrogen peroxide. As illustrated in Table 2, the control oral care composition (1) included a conventional orally acceptable vehicle or liquid carrier, namely, a combination polyethylene glycol and glycerin, and a conventional abrasive system, namely, calcium pyrophosphate. As further illustrated in Table 2, the test oral care compositions (2)-(4) included propylene glycol and the PPO/PEO block copolymer, namely, L-35® as the orally acceptable vehicle or liquid carriers. Particularly, at least a portion of the propylene glycol and glycerin was replaced with the PPO/PEO block copolymer. The test oral care compositions (2)-(4) further included an abrasive system including calcium pyrophosphate and/or sodium metaphosphate in varying amounts and ratios.

TABLE 2

Contents of Control (1) and Test (2)-(4) Oral Care Compositions

| Ingredient | (1) | (2) | (3) | (4) |
|---|---|---|---|---|
| Propylene glycol | 40.21 | 23.58 | 23.88 | 25.505 |
| Polyethylene glycol 600 | 10.00 | — | — | — |
| Glycerin | 2.50 | — | — | — |
| PPO/PEO block copolymer, L-35 ® | — | 23.58 | 23.88 | 25.505 |
| Sodium Metaphosphate | — | 12.50 | 15.00 | 15 |
| Calcium Pyrophosphate | 15.00 | 7.50 | 4.00 | — |
| Viscosity Control Agent | 10.00 | 7.50 | 7.5 | 7.50 |
| Cross-linked PVP complexed with hydrogen peroxide | 11.00 | 11.00 | 11.00 | 11.00 |
| Polymer | 1.75 | 4.25 | 5.00 | 5.50 |
| Thickener | 1.75 | 3.00 | 2.75 | 3.00 |
| Excipients (Flavor, Surfactants, Sweeteners, Fluoride, Antioxidants, Anticalculus and Tartar Control Agents, Polymers) | 7.79 | 7.09 | 6.99 | 6.99 |
| Total | 100 | 100 | 100 | 100 |

The stability of the oral care compositions (1)-(4) was evaluated under accelerated aging conditions. Particularly, each of the oral care compositions (1)-(4) was aged in an incubator maintained at 40° C. and 75% Relative Humidity (RH) for 3 months (16 weeks).

The stability of each of the oral care compositions (1)-(4) was evaluated by determining the amount of hydrogen peroxide (HP) contained in each of the oral care compositions (1)-(4) before and after exposure to accelerated aging conditions for 16 weeks. The amount of HP contained in each of the oral care compositions (1)-(4) was determined via active titration (i.e., Iodometric Titration). Particularly, about 1.3 g of each oral care composition (1)-(4) was measured in respective beakers. 25 ml of glacial acetic acid was then added to each of the beakers, followed by 50 ml of an ethanol/water (1:1 v/v) solution. The resulting solution was stirred or agitated until a paste/gel was fully suspended from the mixture. Then, 5 ml of a 20 weight % potassium iodide solution and four drops of an ammonium molybdate solution/catalyst were added, and the resulting mixture was mixed for 5 minutes (min), resulting in a yellow or yellow tinted solution. 2 ml of a starch indicator was then added to each of the yellow solutions, thereby turning the yellow solution brown in color. The brown solution/mixture was then titrated with a 0.1N sodium thiosulfate solution until the brown color dissipated, leaving a clear solution. The amount (ml) of the sodium thiosulfate solution used was then recorded and used to determine the amount of HP (weight %) in each of the oral care compositions (1)-(4). The results of the active titration are summarized in Table 3.

TABLE 3

Reduction of Hydrogen Peroxide in Oral Care Compositions (1)-(4) After 16 Weeks of Accelerated Aging Conditions

| | (1) | (2) | (3) | (4) |
|---|---|---|---|---|
| Decrease in HP (%) | 9% | 0.5% | 1.5% | 4% |

As indicated in Table 3, all three oral care compositions (2)-(4) exhibited relatively greater peroxide stability as compared to the control oral care compositions (1). Particularly, a relatively smaller decrease in hydrogen peroxide was exhibited in each of the test oral care compositions (2)-(4) as compared to the control oral care composition (1) after exposure to accelerated aging conditions.

Example 2

The pellicle cleaning ratio (PCR) of each of the oral care compositions (1)-(4) of Example 1 was evaluated. It should be appreciated that the PCR is a measure of the cleaning characteristics of a dentifrice with values of from about 40 to about 200, and preferably values of from about 60 to about 200. The PCR values were determined according to the methods detailed and discussed in "In Vitro Removal of Stain with Dentifrice," G. K. Stookey, et al., *J. Dental Res.*, 61, 1236-9, 1982, the contents of which are incorporated herein by reference. The results of the PCR analysis are summarized in Table 4.

TABLE 4

Pellicle Cleaning Ratio (PCR) Scores of Oral Care Compositions (1)-(4)

|     | (1) | (2) | (3) | (4) |
| --- | --- | --- | --- | --- |
| PCR | 96  | 88  | 81  | 75  |

As illustrated in Table 4, the oral care composition (4), which included only sodium metaphosphate exhibited a significantly lower PCR value than the control oral care composition (1), thereby indicating that the oral care composition (4) had a relatively lower stain removal capability as compared to the control oral care composition (1). The remaining oral care compositions (2) and (3), however, had PCR values that were not statistically and/or significantly different from the control oral care composition (1), which indicated that their stain removal capability are comparable to the control oral care composition (1).

Example 3

The compatibility of PPO/PEO block copolymers with hydrogen peroxide, namely, a cross-linked PVP complexed with hydrogen peroxide was evaluated. To evaluate the compatibility, 83.5 weight % of varying PPO/PEO block copolymers, namely, PLURONIC L35®, PLURONIC L64®, and PLURONIC L44®, were combined with 16.5 weight % of the cross-linked PVP complexed with hydrogen peroxide. A control including 16.5% of the cross-linked PVP complexed with hydrogen peroxide and 83.5 weight % of propylene glycol was also prepared for comparison. Each of the samples were then aged for up to 6 weeks under accelerated aging conditions at 60° C. The amount of hydrogen peroxide (HP) contained in each of the oral care compositions (1)-(4) before and after exposure to accelerated aging conditions for 16 weeks was determined, and the results are summarized in Table 5.

TABLE 5

Reduction of Hydrogen Peroxide After 6 Weeks Under Accelerated Aging Conditions

| | Decrease in HP (%) | | | |
| --- | --- | --- | --- | --- |
| Weeks | Control/PG | L35 | L64 | L44 |
| 0 | 0 | 0 | 0 | 0 |
| 1 | 9 | 4.2 | 0.7 | 2 |
| 2 | 51 | 5.8 | 6.4 | 2.7 |
| 4 | 73 | 5.8 | 5.6 | 5.3 |
| 6 | 96 | 6.2 | — | — |

As indicated in Table 5, replacing at least a portion of the conventional orally acceptable vehicle, propylene glycol, with the PPO/PEO block copolymers facilitated or increased peroxide stability.

Example 4

The stability of oral care compositions (5)-(7) of Table 6, including varying abrasives and orally acceptable vehicles, was evaluated via a bloating study. Particularly, propylene glycol was combined with calcium pyrophosphate to prepare oral care composition (5), PLURONIC L35® was combined with calcium pyrophosphate to prepare oral care composition (6), and PLURONIC L35® was combined with sodium metaphosphate to prepare oral care composition (7) according to Table 6.

TABLE 6

| Material | PG + CalPyro (5) | L35 + CalPyro (6) | L35 + SMP (7) |
| --- | --- | --- | --- |
| Propylene glycol | 53.06 | 23.68 | 24.00 |
| PPO/PEO block copolymer, L-35 | — | 23.68 | 24.01 |
| Sodium metaphosphate | — | — | 15.00 |
| Calcium pyrophosphate | 15.00 | 15.00 | — |
| PEG/PPG copolymer | 7.50 | 7.50 | 7.50 |
| Cross-linked PVP:HP Complex | 16.50 | 16.50 | 16.50 |
| Polyvinyl pyrolidone | — | 2.00 | 2.00 |
| Fumed silica | 0.35 | 3.50 | 3.50 |
| Flavor | 2.25 | 2.25 | 2.25 |
| Tetrasodium pyrophosphate | 1.00 | 1.25 | 1.30 |
| Sodium lauryl sulfate | 2.00 | 2.00 | 2.00 |
| Sodium acid pyrophosphate | 0.70 | 1.00 | 0.30 |
| Sodium monofluorophosphate | 0.76 | 0.76 | 0.76 |
| Sodium saccharin | 0.80 | 0.80 | 0.80 |
| Sucralose | 0.05 | 0.05 | 0.05 |
| Butylated hydroxytoluene | 0.03 | 0.03 | 0.03 |
| Total | 100 | 100 | 100 |

The stability of the oral care compositions (5)-(7) were evaluated under accelerated aging conditions. Particularly, each of the oral care compositions (5)-(7) were aged in an incubator maintained at 40° C. and 75% Relative Humidity (RH) for up to 21 weeks. To test the stability via bloating, each of the oral care compositions (5)-(7) was disposed in a standard crimped dentifrice tube. Each of the tubes were marked approximately 40 mm from the bottom of a crimp of the tube to indicate the point of measurement. Measurements of the bloating were conducted by measuring the respective width or thickness of each of the tubes with a digital caliper positioned at the point of measurement and at an angle parallel to the crimp of the tube. The results of the stability of the oral care compositions are summarized in Table 7.

TABLE 7

Bloating of Oral Care Compositions (5)-(7) After Aging at 40° C.

| Week | Bloating (mm) (5) | (6) | (7) |
|---|---|---|---|
| 0 | 0 | 0 | 0 |
| 4 | 2.41 | 1.0375 | 1.12 |
| 8 | 2.32 | 2.9875 | 1.52 |
| 12 | 4.03 | 3.6975 | 2.8 |
| 13 | 6.86 | 3.1875 | 2.24 |
| 14 | 7.46 | 3.7875 | — |
| 15 | 8.06 | 4.2815 | 2.32 |
| 16 | 9.96 | 3.8875 | 2.78 |
| 17 | — | 4.6875 | 2.32 |
| 18 | — | 6.1175 | 2.54 |
| 19 | — | 7.0975 | 3 |
| 21 | — | — | 2.4 |

As indicated in Table 7, the oral care composition (5) including propylene glycol and calcium pyrophosphate was the least stable composition, followed by the oral care composition (6) including L35 and calcium pyrophosphate; and the most stable was the oral care composition (7) including the L35 and sodium metaphosphate.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition, comprising:
an orally acceptable vehicle comprising
a block copolymer of ethylene oxide and propylene oxide having an average molecular weight greater than or equal to about 1,000 Da and less than or equal to about 3,000 Da;
a peroxide whitening agent; and
an abrasive system comprising at least one insoluble phosphate salt;
wherein the block copolymer is present in an amount from 20 weight % to 40 weight % based on a total weight of the oral care composition;
wherein the pellicle cleaning ratio of the composition is greater than or equal to 80.

2. The oral care composition of claim 1, further comprising water in an amount less than 5 weight %, less than 3 weight %, less than 1.0 weight %, less than 0.1 weight %, less than 0.05 weight %, less than 0.01 weight %, less than 0.005 weight %, or less than 0.0001 weight %, based on a total weight of the oral care composition.

3. The oral care composition of claim 1, wherein the orally acceptable vehicle further comprises a humectant, wherein the humectant comprises at least one of glycerin, propylene glycol, polyethylene glycol, and combinations thereof.

4. The oral care composition of claim 1, wherein the orally acceptable vehicle further comprises propylene glycol.

5. The oral care composition of claim 1, wherein the block copolymer of ethylene oxide and propylene oxide is represented by formula (ethylene oxide)$_x$-(propylene oxide)$_y$-(ethylene oxide)$_z$, wherein:
x is an integer from about 5 to about 15,
y is an integer from about 10 to about 20, and
z is an integer from about 5 to about 15.

6. The oral care composition of claim 1, wherein the block copolymer of ethylene oxide and propylene oxide is represented by formula (ethylene oxide)$_{11}$(propylene oxide)$_{16}$(ethylene oxide)$_{11}$.

7. The oral care composition of claim 1, wherein the orally acceptable vehicle comprises propylene glycol and the block copolymer of ethylene oxide and propylene oxide in a weight ratio of from about 0.9:1 to about 1.1:1.

8. The oral care composition of claim 1, wherein the abrasive system comprises at least one of sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, or mixtures thereof.

9. The oral care composition of claim 1, wherein the abrasive system comprises sodium metaphosphate, calcium pyrophosphate, or mixtures thereof.

10. The oral care composition of claim 8, wherein a weight ratio of the sodium metaphosphate to the calcium pyrophosphate is from about 0.5:1 to about 2.9:1.

11. The oral care composition of claim 1, wherein the abrasive system is present in an amount of from about 5 weight % to about 40 weight % based on a total weight of the oral care composition.

12. A method for whitening teeth, comprising contacting the oral care composition of claim 1 with a surface of the teeth.

13. A method for preventing stains on teeth, comprising contacting the oral care composition of claim 1 with a surface of the teeth.

14. A method for increasing peroxide stability in an oral care composition, the method comprising:
replacing at least a portion of the propylene glycol and glycerin with a block copolymers of ethylene oxide (EO) and propylene oxide (PO) represented by formula (ethylene oxide)$_{11}$(propylene oxide)$_{16}$(ethylene oxide)$_{11}$; and
combining the orally acceptable vehicle with an abrasive system comprising a combination of sodium metaphosphate and calcium pyrophosphate;
wherein the pellicle cleaning ratio of the composition is greater than or equal to 80.

* * * * *